(12) United States Patent
Puolakanaho et al.

(10) Patent No.: US 6,361,502 B1
(45) Date of Patent: Mar. 26, 2002

(54) NON-INVASIVE MEASURING DEVICE WITH DIFFERENT OPERATING MODES

(75) Inventors: Pertti Puolakanaho, Oulu; Erkki Loponen, Ruukki; Urpo Niemelä; Pekka Rytky, both of Oulu, all of (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 09/424,282

(22) PCT Filed: May 20, 1998

(86) PCT No.: PCT/FI98/00427

§ 371 Date: Nov. 19, 1999

§ 102(e) Date: Nov. 19, 1999

(87) PCT Pub. No.: WO98/55022

PCT Pub. Date: Dec. 10, 1998

(30) Foreign Application Priority Data

May 21, 1997 (FI) .................................. 972173

(51) Int. Cl.[7] .................................. A61B 5/02
(52) U.S. Cl. ........................ 600/508; 600/502
(58) Field of Search ............................ 600/300, 301, 600/386, 390, 481, 483, 484, 500–503, 508

(56) References Cited

U.S. PATENT DOCUMENTS 4,543,957 A * 10/1985 Friedman et al.
5,738,104 A * 4/1998 Lo et al.

* cited by examiner

Primary Examiner—Mark Bockelman
(74) Attorney, Agent, or Firm—Hoffman & Baron, LLP

(57) ABSTRACT

The invention relates to a measuring device (102) carried by a user during exercise for measuring non-invasively at least one signal from the body, e.g. a wireless heart rate monitor, and to a method of controlling same. The measuring device comprises a user interface (120). The user interface comprises selection means (114), e.g. push buttons (114), and display means (116, 122), e.g. a liquid crystal display. The user interface (116) displays different operating modes, e.g. a watch mode (300), a set mode (306) and an operating mode (302) for measuring a signal from the body. The operating modes are arranged as a main loop sequence (300-302-304-306). The operating modes have different sub-operating modes for displaying parameters associated with exercising. The sub-operating modes are arranged as sub-loop sequences (400-404-406-410) under each operating mode. In accordance with the invention, the user is able to configure the sub-loop sequence (400-404-406-410) by the selection means (114).

46 Claims, 8 Drawing Sheets

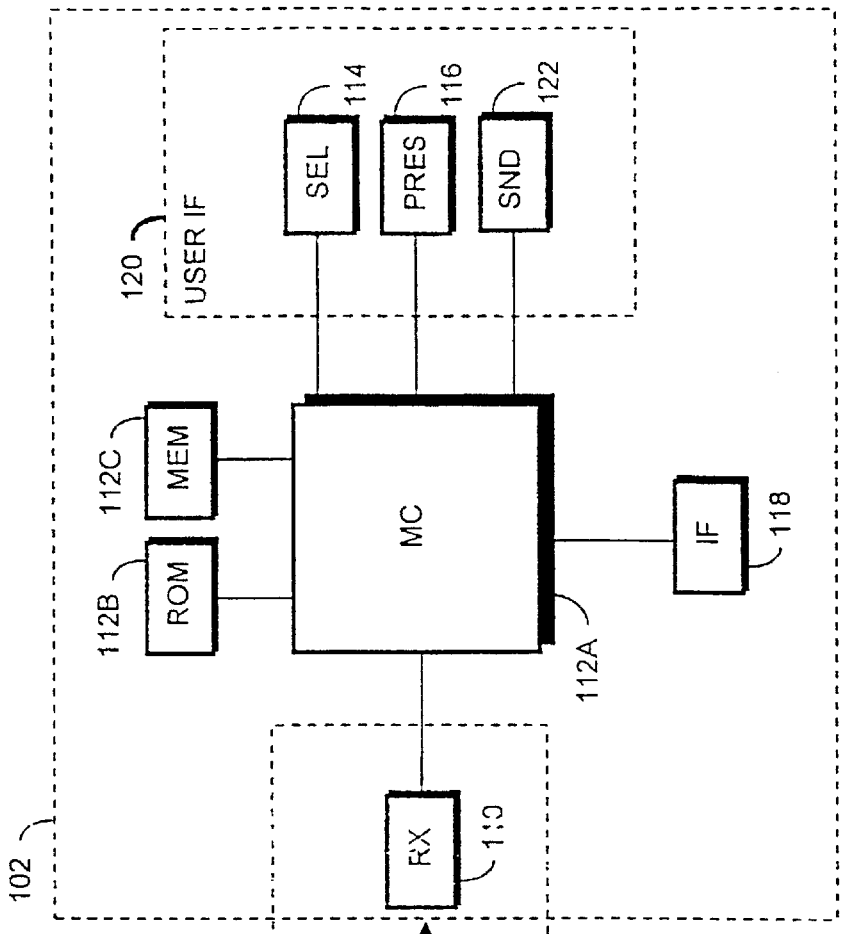
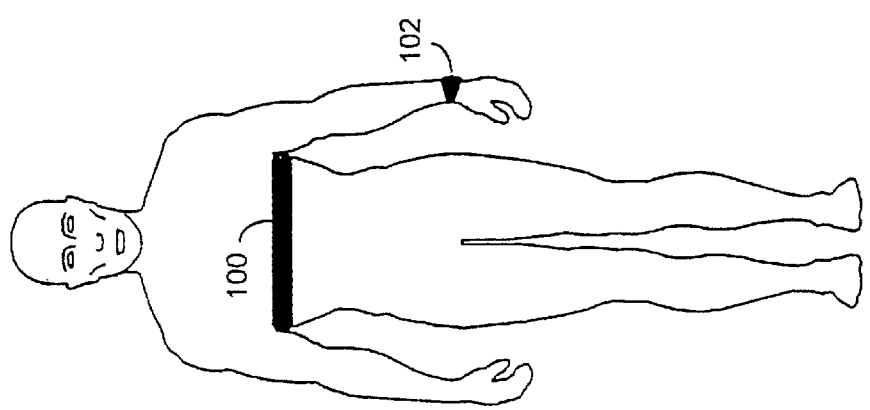
Fig 1B
Fig 1A

NON-INVASIVE MEASURING DEVICE WITH DIFFERENT OPERATING MODES

FIELD OF THE INVENTION

The invention relates to a measuring device carried by a user during exercise for measuring non-invasively at least one signal from the body, the measuring device comprising:
- a measuring unit for measuring at least one signal from the body,
- a user interface comprising selection means for making selections, and display means for displaying data,
- a control unit communicating with the measuring unit and the user interface for controlling and monitoring the operation of the measuring device,
- the interface comprising various operating modes comprising at least a watch mode, a set mode, and at least one operating mode for measuring a signal from the body, the operating modes being arranged as a main loop sequence,
- the operating modes comprising various sub-operating modes for displaying parameters associated with exercising, the sub-operating modes being arranged as sub-loop sequences under each operating mode.

DESCRIPTION OF RELATED ART

Various portable personal measuring devices for measuring a signal of the user's choice from the body have been designed during the last few years, Devices have been designed for different end users: persons concerned with their health, fitness enthusiasts, goal-oriented athletes and sports champions.

Signals to be measured include e.g. heart rate and arterial blood pressure. These measurements can be carried out non-invasively, i.e. the measuring sensors are disposed on a person's skin. Hence the use of meters is safe and suitable for everyone.

A measuring device designed for measuring heart rate, i.e. a heart rate monitor, for example, is employed to improve physical and mental condition efficiently and safely. The user can employ a heart rate monitor to monitor his heart rate level during exercising, for example, and avoid excessive stress. A heart rate monitor can also be utilized in slimming since it has been scientifically shown that the most efficient way to burn fat stored in the body is to exercise at a given heart rate (about 55 to 65%) of a person's maximum heart rate. The maximum heart rate is calculated e.g. by subtracting the person's age from 220, or the maximum heart rate can also be measured.).

In U.S. Pat. No. 4,625,733 Säynäjäkangas teaches a wireless and continuous heart rate measuring concept employing a transmitter attached to a user's chest for ECG accurate measuring of the user's heart rate and for telemetric transfer of heart rate data to a heart rate receiver attached to the user's wrist by employing magnetic coils in the transfer.

In addition to a receiver, the unit attached to the wrist comprises a control unit and a user interface. The control unit controls and monitors the operation of the measuring device. The necessary heart rate data processing is also carried out in the control unit. The control unit is typically a microprocessor also comprising an ROM memory in which the software of the measuring device is stored. The control unit can also comprise separate memory in which measurement data generated during the use of the device can be stored for further processing. For further processing, the data can be transferred to a separate personal computer.

The user interface of a heart rate monitor comprises selection means for making selections, and display means for displaying data. The selection means are typically push buttons. The number of buttons may vary, typically totalling three separate buttons. In addition, a so-called wireless button can be used. This means that the user selects the desired function, e.g. the start of measurement, by a special operation, e.g. by bringing the transmitter and the receiver close to one another. This closeness is detected in the magnetic coils on account of the changes which their closeness causes in the magnetic field. A conventional liquid crystal display typically serves as the display means.

The user operates the heart rate monitor by pressing the buttons. The heart rate monitor provides feedback on its display as text, numbers and various symbols.

The basic structure of the user interface in nearly all known heart rate monitors comprises different operating modes. A heart rate monitor usually comprises at least a watch mode and a heart rate measurement mode. In watch mode the heart rate monitor operates as a normal wrist watch. An operating mode may also have sub-operating modes somehow associated with the operating mode. In sub-operating modes, different parameters associated with exercising are displayed to the user. The time of day is a parameter indicating real exercise time. The date can be displayed. An alarm clock type of sub-operating mode is also common.

Different parameters measured for the exercise are displayed in heart rate measurement mode. Examples of sub-operating modes are e.g. exercise time and heart rate, real exercise time and heart rate, effective exercise time and heart rate, energy consumed by the user in the exercise and heart rate. In heart rate measurement mode the user can also be controlled by means of sound signals and symbols displayed on the display. The control may aim at keeping the exercise within effective and safe limits (typically within the range 55 to 85% of a person's maximum heart rate). In this case the user himself typically sets the lower and upper limits for his heart rate. The limits are established on the basis of information obtained in medical studies. During exercise, the measuring device gives an alarm if the heart rate exceeds the upper limit or falls below the lower limit.

The operating modes often also comprise a set mode. The set mode allows the user to set functions controlling and facilitating the exercise, e.g. said lower and upper limits for the heart rate.

The operating modes may also comprise a file mode. This is subject to the device comprising memory for storing data during exercise in the manner described above. In file mode the stored data can be studied and analyzed later.

The described device to be attached to the wrist is small, which limits the size of the buttons and the display. However, the data displayed on the display have to be presented by large enough letters, numbers or symbols to allow easy detection thereof by the main groups of the device. When running, for example, the user has to be able to swiftly perceive the information on the display, often for traffic safety reasons alone. The effectiveness of the exercise falls if the user has to interrupt the exercise in order to use the device, since the heart rate starts to fall when the user is standing still. This is why the display should not show too much information at the same time.

Another problem is associated with the buttons. The sizes of the buttons have to be sufficient for example for a skier wearing ski gloves to be able to operate the device. Neither should there be too many buttons, since the user may have difficulty in learning their operation.

The user interface employs symbolics and a complex operating logic, the learning of which requires of the user high motivation and that he acquaint himself with the operator's manual.

When using the device, the user is typically engaged in an exercise of the duration of perhaps several hours, and is not necessarily carrying the manual with him. If a problem arises, the user may be frustrated, in the worst case the stored measurement results may even be lost because of faulty operation of the device by the user.

Although the device in itself, objectively assessed, seems easy to use, the above reasons may have made it tedious and difficult for the user to learn to operate the device and form an internal model in his mind for the use of the device.

CHARACTERISTICS OF THE INVENTION

It is the object of the present invention to provide a measuring device of the type described, the use of which is easier to learn than that of present measuring devices. The invention particularly relates to the user interface of the measuring device.

This is achieved by a measuring device of the type described in the introduction, characterized by the control unit being adapted to configure the sub-loop sequence in accordance with selections the user makes by the selection means and to display by the display means the sub-loop sequence configured by the user.

The invention further relates to a method of controlling a measuring device carried by a user during exercise for measuring non-invasively at least one signal from the body, the measuring device comprising

- a measuring unit for measuring at least one signal from the body,
- a user interface comprising selection means for making selections, and display means for displaying data,
- a control unit communicating with the measuring unit and the user interface for controlling and monitoring the operation of the measuring device,
- the interface comprising various operating modes comprising at least a watch mode, a set mode, and at least one operating mode for measuring a signal from the body, the operating modes being arranged as a main loop sequence,
- the operating modes comprising various sub-operating modes for displaying parameters associated with exercising, the sub-operating modes being arranged as sub-loop sequences under each operating mode.

In accordance with the invention the method is characterized in that the user utilizes the user interface to configure the sub-loop sequence.

The method and measuring device of the invention provide significant advantages. It is easier and faster for a user to learn how to operate the device. The user can use the feature he needs during the exercise. The user does not have to use the features he considers unnecessary. The measuring device is simpler from the point of view of the user. New features can be easily added to the measuring device when required. The new features are mainly software-based and can be added as software upgrades to devices in the users' possession. On the other hand, it is easy to improve the design and production of the device since the HW parts of the device remain the same or almost the same while mainly the software only is subject to changes.

DESCRIPTION OF THE DRAWINGS

In the following the invention will be described in greater detail with reference to examples according to the attached drawings, in which FIG. 1A shows how a user typically carriers a measuring device with himself, and FIG. 1B is a block diagram of a more detailed structure of a measuring device.

DESCRIPTION OF THE PREFERRED EMBODIMENTS

Figure 2:
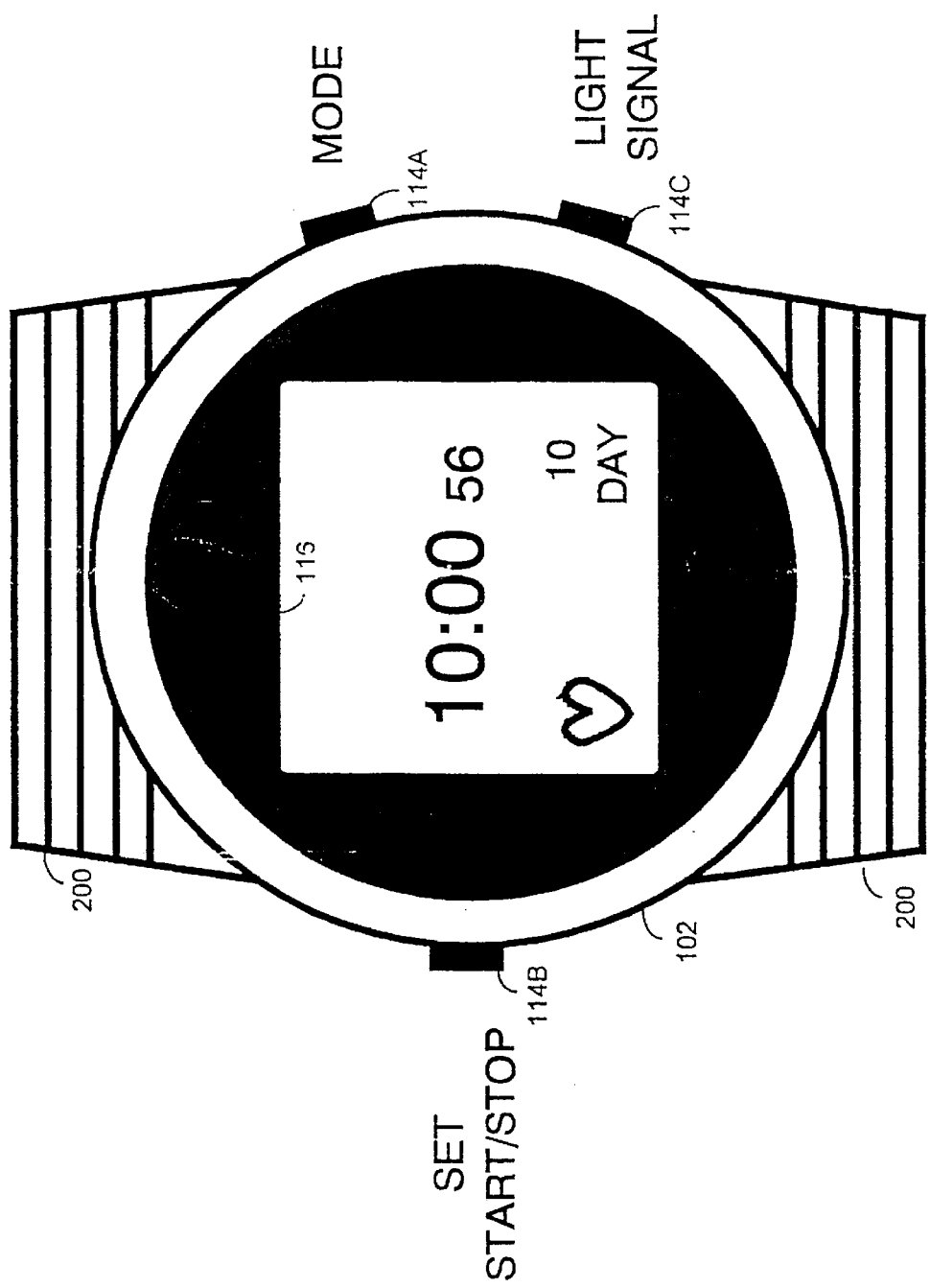
FIG. 2 shows a typical user interface of a measuring device.

The present invention is suitable for use in all types of measuring devices, which are carried by a user during exercise for measuring non-invasively at least one signal from the body, in e.g. heart rate monitors, and even in advanced versions of heart rate monitors in which e.g. the user's energy consumption, blood pressure etc. are measured in addition to or instead of the heart rate.

FIGS. 1A and 1B illustrate a preferred embodiment of the present invention, a heart rate monitor. A heart rate monitor 102 typically comprises a measuring unit 104 and a control unit 112A controlling the measuring unit. The control unit 112A also controls a user interface 120 comprising selection means 114 and display means 116. The control unit 112A is typically a microprocessor comprising an ROM memory 112B in which the software controlling the device is stored. The device may further comprise additional memory 112C, in which information on e.g. heart rate, gathered during the measurement, can be stored. In principle the control unit can also be implemented by an ASIC circuit or by another coupling composed of HW units. Thus the changes according to the invention in the measuring device are preferably changes in the software of the device.

The measuring unit 104 may be one piece, e.g. a heart rate monitor carried on the wrist, the heart rate being measured from the wrist. However, a better measurement result is obtained by present technology by using a solution of the type described, in which the measuring unit 104 is divided into two parts: a wireless transmitter 100 that is attached around the chest and measures the heart rate, and a heart rate receiver 110 attached to the wrist.

FIG. 2 shows a typical heart rate monitor user interface. A wrist watch type of heart rate monitor 102 is attached to a wristband 200. A liquid crystal display 116 is used as the display means. In the figure, the liquid crystal display 116 displays in watch mode the time of day, 10:00.56, and the day of month, 10. The display also displays a heart symbol for indicating whether heart rate measurement is active. The three push buttons 114A, 114B and 114C shown in the figure constitute the selection means. Button 114A (MODE) is intended for shifting between the different modes and displays. Button 114B (SET, START/STOP) is used for making selections and for starting and stopping functions. Button 114C (LIGHT, SIGNAL) is intended for adjusting the settings and for using the background light of the display 116 and the sound signal during the measurement function.

In addition a wireless button can be used which is based on magnetic induction and is activated by bringing close to each other the heart rate receiver 110 comprised by the heart rate monitor 102 and the transmitter 110 to be attached around the chest. The operating principle is described in greater detail in U.S. Pat. No. 5,486,818. By the operation of the wireless button it is possible e.g. to display an additional display or switch on the background light illuminating the display 116 in measurement mode.

The measuring device may allow the user e.g. to program a short-cut function for a selection means in set mode. This short-cut allows the user to rapidly access a frequently used function, e.g. a sub-operating mode.

Another feature facilitating the use is a home selection function. This home option function allows the user to rapidly access the basic mode of the device, e.g. watch mode. Both the short-cut and home selection can be implemented in various ways. An alternative is to simultaneously press several selection means, e.g. two different buttons, to make the selection. Another alternative is to press the button for a long time, e.g. two seconds, after which the selection is made.

The user interface also comprises a sound signal indicating e.g. an alarm, exceeding or falling below the set heart rate limit, or other information relevant to the user. To produce a sound signal, the heart rate monitor 102 comprises a sound unit 122.

The heart rate monitor 102 frequently comprises an interface 118 between the heart rate monitor 102 and the outside world. Information stored in the heart rate monitor can be transferred via the interface 118 to e.g. a personal computer for further processing. The heart rate monitor software can also be updated via the interface 118. This calls for special mechanisms, e.g. the ROM memory 112B in which the software is stored has to be replaced by a write-enable type of memory.

Figure 3A:
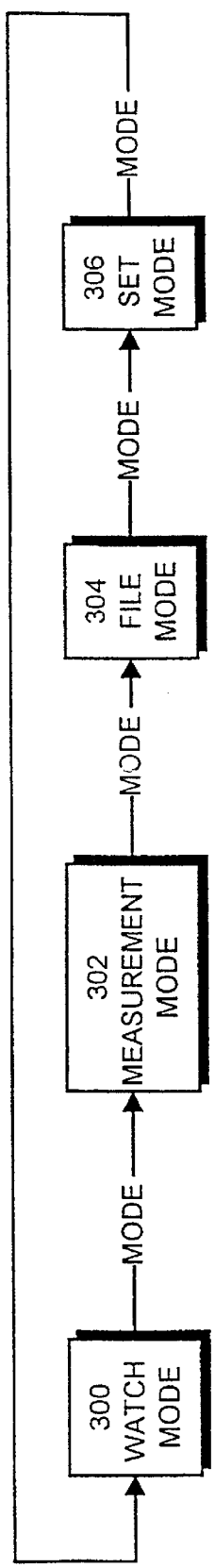
FIG. 3A shows operating modes and shifting between them.

FIG. 3A shows a main loop sequence formed by the operating modes. The user of the heart rate monitor 102 sees the details associated with each operating mode on the display 116. The heart rate monitor 102 typically comprises at least the first two of the following operating modes: a watch mode 300, a heart rate measurement mode 302, a file mode 304 and a set mode 306. As is also shown in FIG. 3, button 114A (MODE) has to be pressed to shift from one operating mode to another. When the user sees the watch mode 300 on the display 116, he can press the MODE button 114A once to access the heart rate measurement mode 302. Thus pressing the MODE button 114A allows the user to advance in one direction in the main loop sequence. From the last set operating mode 306 of the main loop sequence the user again reaches the start, the watch mode 300, by pressing the MODE button 114A.

Figure 4A:
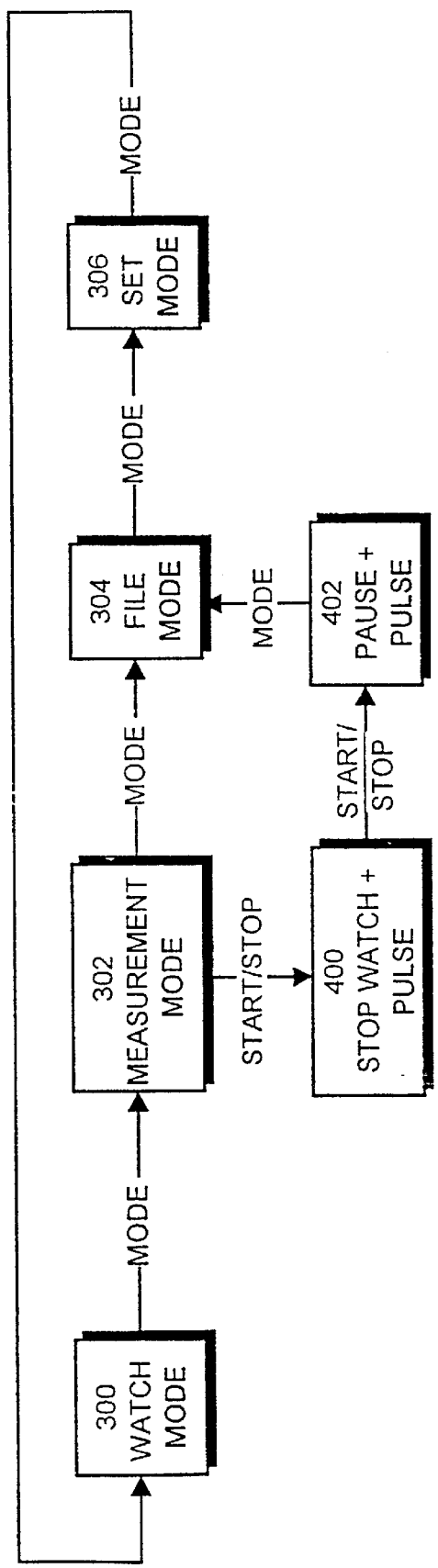
FIG. 4A shows heart rate measurement at its simplest.

FIG. 4A shows how a user, when employing the heart rate monitor 102, typically shifts from one operating mode to another. The user is first in the watch mode 300. The user wants to start an exercise, e.g. a run, and consequently presses once the MODE button 114A to access the heart rate measurement mode 302. Having accessed the heart rate measurement mode 302, the user presses the START/STOP button 114B to access the first suboperating mode 400 of the sub-loop sequence of the heart rate measurement mode 302, displaying exercise time and user heart rate. Having run a while, the user wants to stop the exercise, and consequently presses the START/STOP button 114B again. This gains access to a sub-operating mode 402 of the sub-loop sequence of the heart rate measurement mode 302, displaying exercise time and user heart rate. By pressing The START/STOP button 114B again, the user may continue the exercise, or shift by the MODE button 114A to the next operating mode of the main loop sequence, i.e. the file mode 304.

Figure 4B:
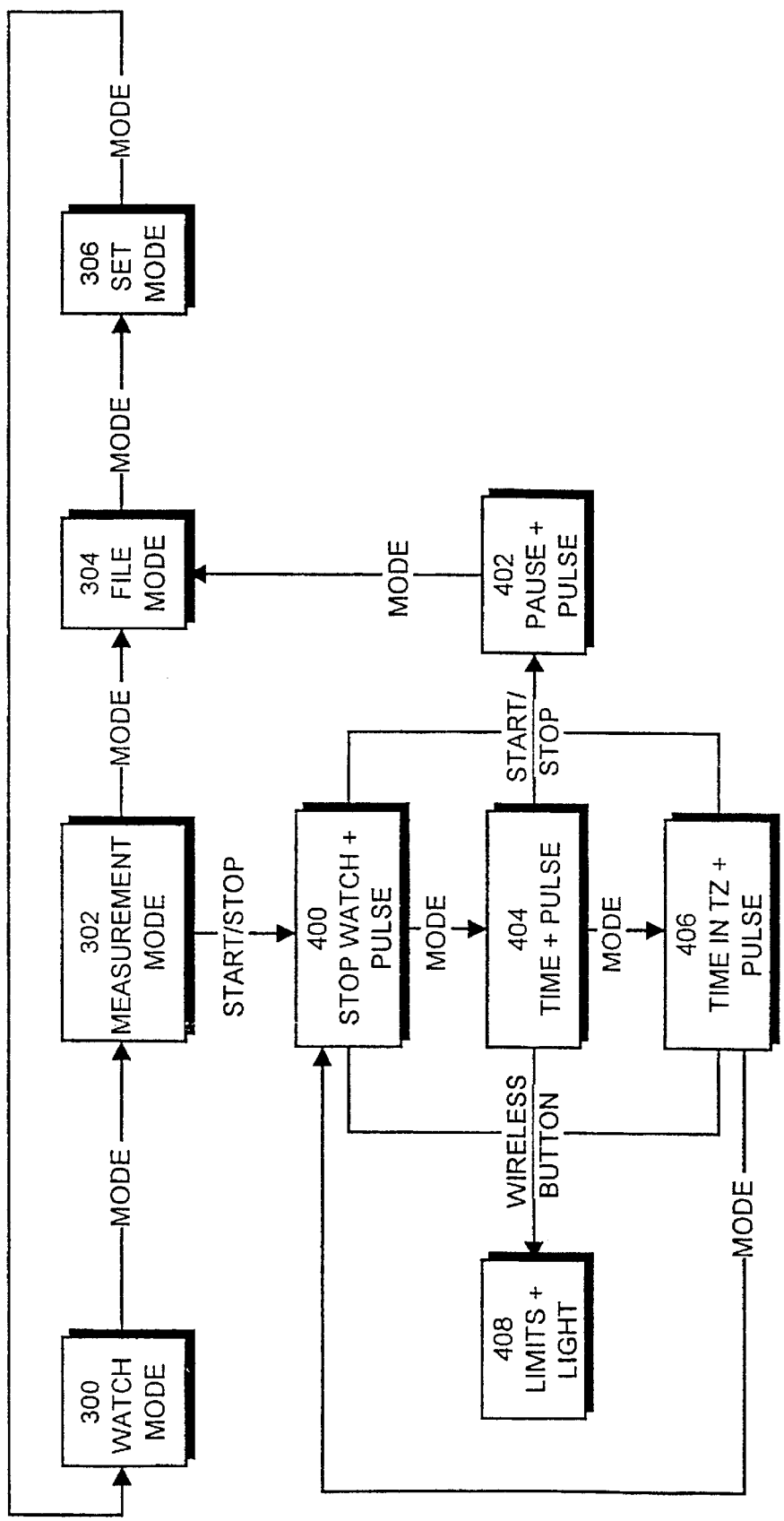
FIG. 4B shows more advanced user heart rate measurement.

FIG. 4B shows how a more experienced user may use the device in a more versatile manner compared with the basic functions of a novice described in FIG. 4A. Thus the user may advance during measurement along the sub-loop sequence of the heart rate measurement mode 302 by pressing the MODE button 114A. The sub-operating mode 404 displays real exercise time and heart rate. The sub-operating mode 406 displays effective exercise time and heart rate. During measurement, access can be gained by the wireless button to the sub-operating mode 408 which displays the set heart rate limits, and allows the background light of the display 116 to be switched on.

Figure 5:
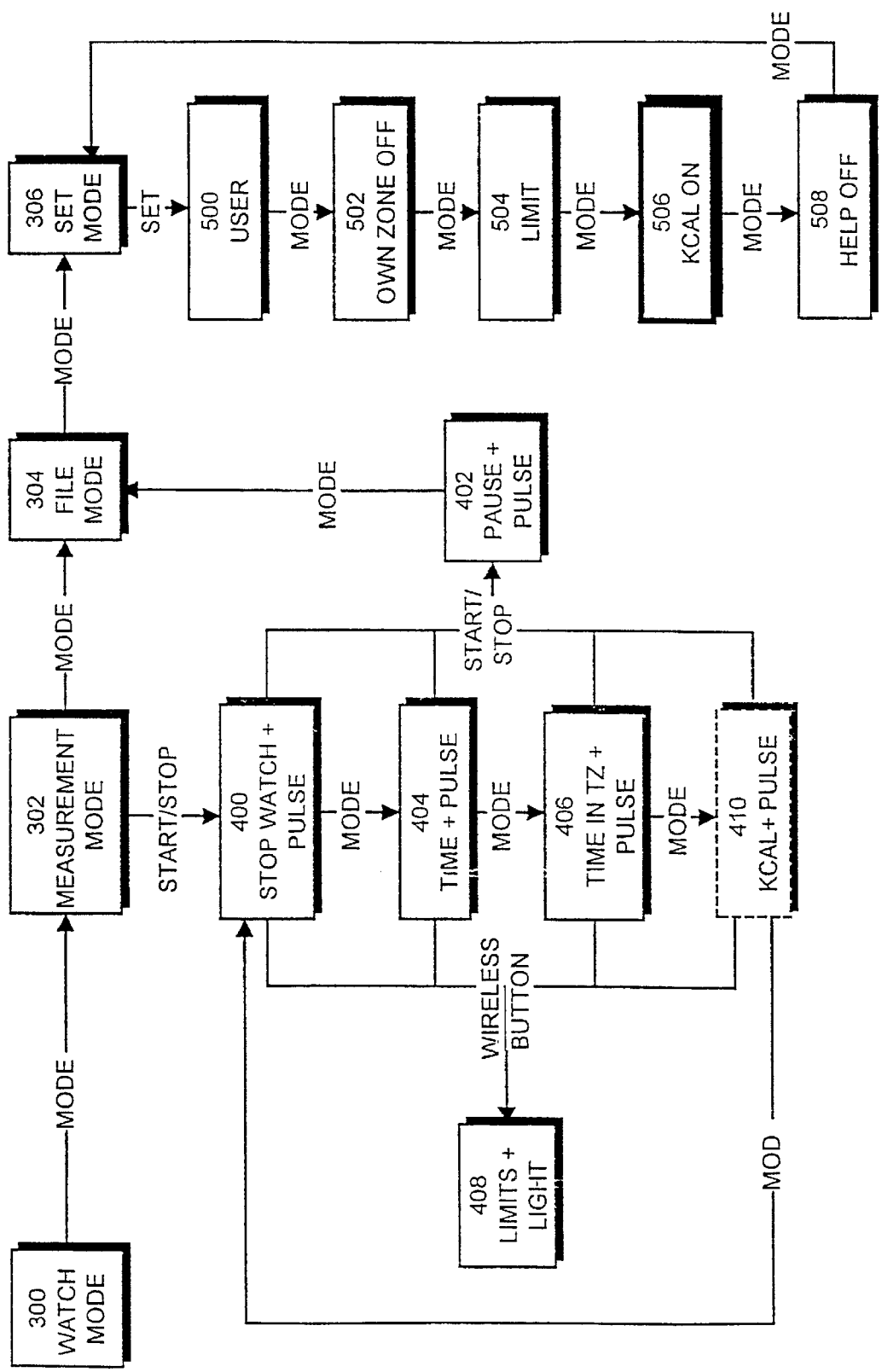
FIG. 5 shows how a new sub-operating mode is added.

In accordance with the invention, the user is able to configure the sub-loop sequence. FIG. 5 shows an example of how configuration is carried out. In the operating modes the MODE button 114A is pressed to access the set mode 306, in which the change of setting is initiated by pressing the SET button 114B. User-specific settings 500 (e.g. age, weight and sex) are first accessed any bypassed by pressing the MODE button 114A. The sub-operating modes automatic setting of heart rate limits 502, limits to be set 504, and calculation of energy consumed by the user 506, are also bypassed without any changes in the settings. In the sub-operating mode 506 the calculation of the energy used by the user is switched on, i.e. from OFF mode to ON mode. As a result the new sub-operating mode 410 for displaying the user's pulse and the energy he consumes during the exercise is added to the sub-loop sequence of the heart rate measurement mode. The user leaves the sub-loop sequence of the set mode by pressing twice the MODE button 114A. He then presses twice the MODE button 114A to shift to the heart rate measurement mode 302. Once heart rate measurement is on, he can, if desired, also check his energy consumption, since the sub-loop sequence configured by him now also comprises calculation of the energy consumed during the exercise and displaying it in the sub-operating mode 410.

The configurations the user makes also affect the parameters to be stored by storage means 112C. In the file mode 304 the stored parameters can be viewed, including e.g. total exercise time, time between heart rate limits, energy consumed by the user during the exercise, and cumulative energy consumed by the user.

Figure 4C:
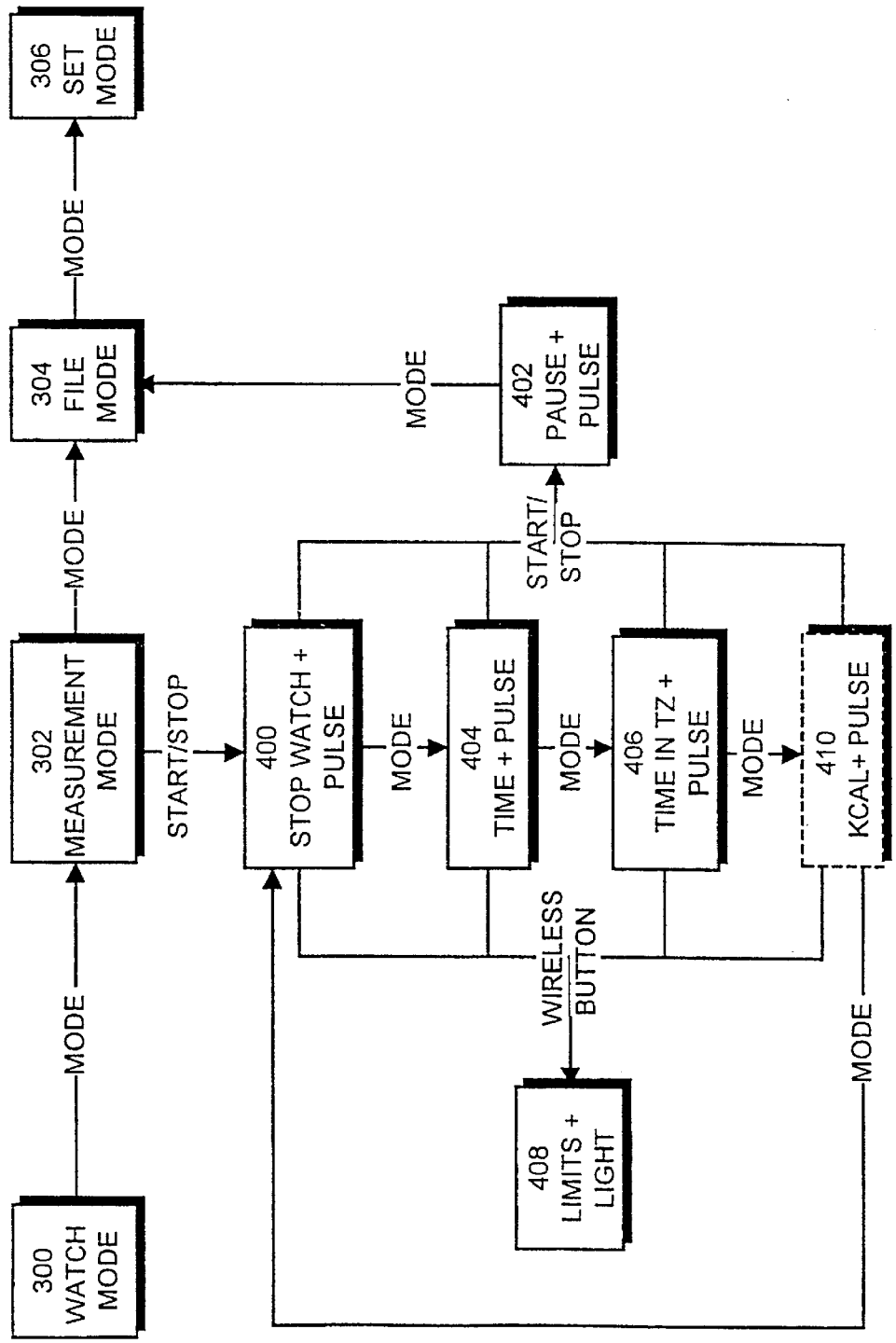
FIG. 4C shows addition of a new sub-operating mode to the heart rate measurement sub-loop sequence in accordance with the invention.

FIG. 4C shows how the addition of a new sub-operating mode described in FIG. 5 can be seen by the user. When FIGS. 4B and 4C are compared, it can be seen that the new sub-operating mode 410 is logically added to the sub-loop sequence of the heart rate measurement mode 302. On the one hand the described solution is easy to implement technically and on the other hand it facilitates learning how to use the device, since the internal model of the device formed by the user is logically modifiable according to the selections made by the user.

Figure 6:
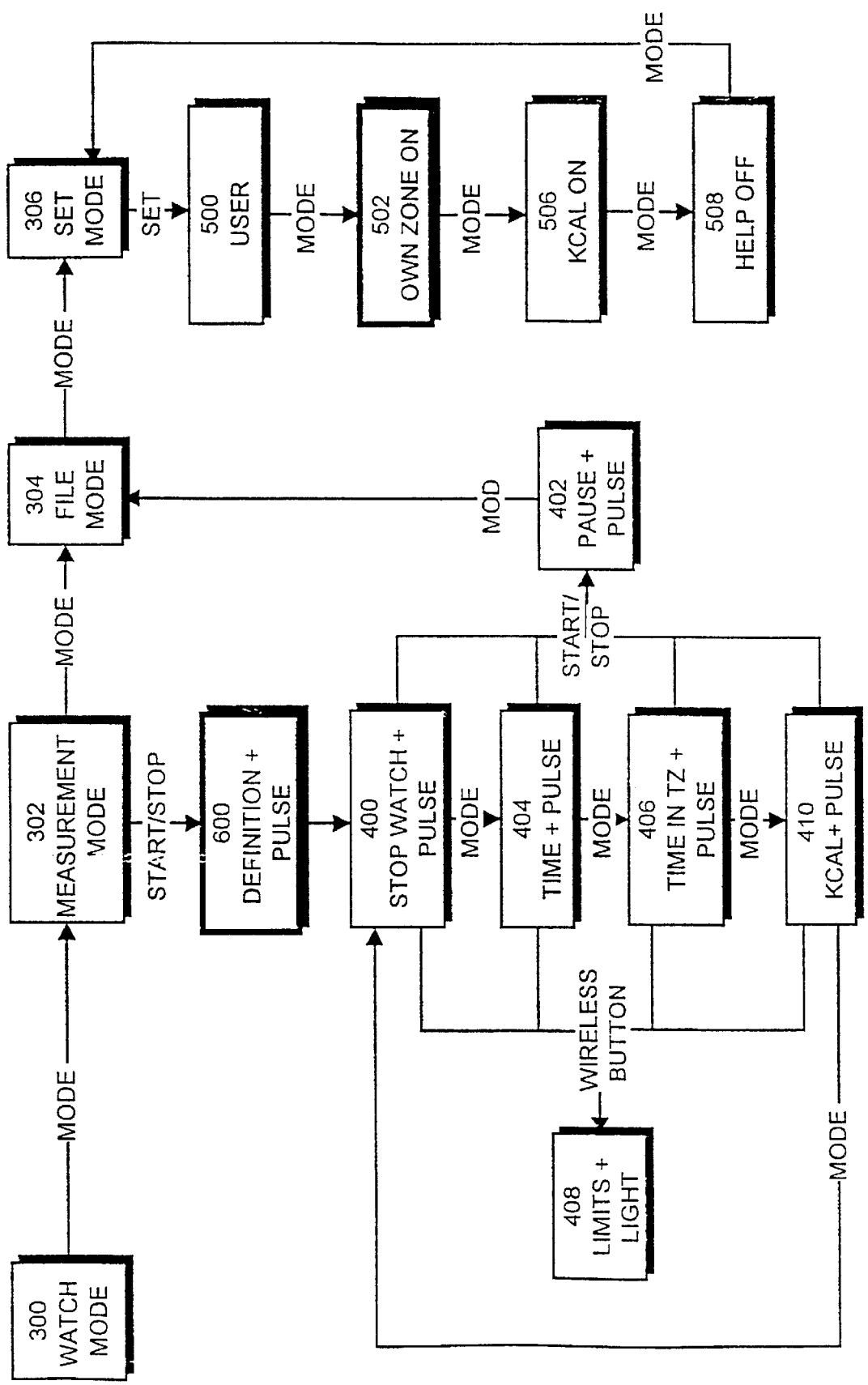
FIG. 6 shows how a sub-operating modes can be mutually exclusive.

FIG. 6 shows how sub-operating modes can be mutually exclusive. In the sub-operating mode 502 of the set mode 302 the user selects the switching on of the automatic setting of heart rate limits, i.e. from OFF mode to ON mode. In this case the sub-operating mode 504, shown in FIG. 5, in which the user himself sets the heart rate limits is not shown to the user in the sub-loop sequence according to FIG. 6, i.e. the sub-operating mode 502 excludes the sub-operating mode 504. FIG. 6 also shows that the sub-loop sequence of the heart rate measurement mode 302 comprises an entirely new sub-operating mode 600 in which the user's heart rate is shown and the user is inquired of the type of exercise he wants to carry out. On the basis of the information received from the user the device then automatically determines the lower and upper limits of the heart rate to be employed in the exercise. As can be seen from FIG. 6, there is no access back to the sub-operating mode 600 by the MODE button 114A. This is practical since a unique function during said measurement process is involved. FIG. 6 also shows that transfer from the sub-operating mode 600 to the sub-operating mode 400 is automatic once the user has carried out the measures required in the sub-operating mode 600.

Figure 3B:
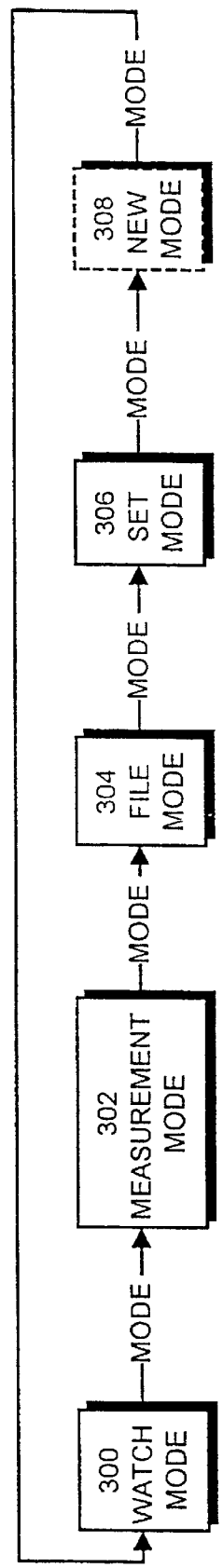
FIG. 3B shows addition of a new operating mode to the main loop sequence in accordance with the invention.

Operating modes can also be added to the main loop sequence. FIG. 3B shows how a new operating mode 308 has been added to the main loop sequence of FIG. 3A after the set mode 306. This feature is very useful for product development, since a new part can easily be added to the software of the heart rate monitor. It may be possible to update a device already in a user's possession. From the point of view of the user, it is also advantageous that the user interface of the device remains the same, with only a slightly lengthening of the main loop sequence.

Although the invention is described herein with the reference to the example in accordance with the accompanying drawings, it will be appreciated that the invention is not to be so limited, but may be modified in a variety of ways within the scope of the inventive idea disclosed in the appended claims.

What is claimed is:

1. A measuring device (102) carried by a user during exercise for measuring non-invasively at least one signal from the body, the measuring device (102) comprising:
    a control unit (112A) for controlling and monitoring the operation of the measuring device (102);
    a measuring unit (104) communicating with the control unit (112A) for measuring at least one signal from the body;
    a user interface (120) communicating with the control unit (112A) comprising:
        selection means (114) for making selections, and
        various operating modes comprising at least a watch mode (300), set mode (306), and at least one operating mode (302) for measuring a signal from the body, the operating modes being arranged as a main loop sequence (300-302-304-306), and
        the operating modes comprising various sub-operating modes for displaying parameters associated with exercising, the sub-operating modes being arranged as sub-loop sequences (400-404-406-410) under each operating mode, and
        display means (116, 122) for displaying data, and the sub-loop sequence (400-404-406-410) is displayed to the user by the display means (116, 122),
    characterized by the control unit (112A) being adapted to configure at least one sub-loop sequence (400-404-406-410) in accordance with selection the user makes by the selection means (114), in which configuration at least one sub-operation mode (410) is connected to be part of the sub-loop sequence (400-404-406-410) or sub-operation mode (410) is disconnected from the sub-loop sequence (400-404-406).

2. A measuring device as claimed in claim 1, characterized in that the control unit (112A) is adapted to operate in such a way that a sub-operating mode (502) excludes another sub-operating mode (504).

3. A measuring device as claimed in claim 1, characterized in that the control unit (112A) is adapted to add a new operating mode (308) to the main loop sequence (300-302-304-306).

4. A measuring device as claimed in claim 1, characterized in that the control unit (112A) is adapted to add a new sub-operating mode (410) to the sub-loop sequence (400-404-406).

5. A measuring device as claimed in claim 1, characterized in that the control unit (112A) is adapted to configure the main loop sequence (300-302-304-306-308) in accordance with the selections made by the user by the selection means (114) and to display by the display means (116) the main loop sequence (300-302-304-306-308) according to the user's selection.

6. A measuring device as claimed in claim 1, characterized in that the control unit (112A) is adapted to perform the configuration in the set mode (306).

7. A measuring device as claimed in claim 1, characterized in that the control unit (112A) is adapted to perform an ON/OFF type of configuration for each sub-operating mode.

8. A measuring device as claimed in claim 1, characterized in that the measuring device comprises short-cut means for fast selection of a sub-operating mode.

9. A measuring device as claimed in claim 1, characterized in that the measuring device comprises home selection means for fast selection of the basic mode.

10. A measuring device as claimed in claim 1, characterized in that the selection means (114) are push buttons (114A, 114B, 114C).

11. A measuring device as claimed in claim 1, characterized in that the display means (116) are a liquid crystal display.

12. A measuring device as claimed in claim 1, characterized in that the sub-operating modes of the watch mode (300) comprise: setting of alarm time, setting of time of day, setting of date.

13. A measuring device as claimed in claim 1, characterized in that the signal to be measured is user heart rate, the operating mode (302) measuring the signal from the body is heart rate measurement mode, and the measuring device is a heart rate monitor.

14. A measuring device as claimed in claim 13, characterized in that the measuring unit (104) comprises a wireless transmitter (100) to be attached to the chest and a wireless heart rate receiver (110) to be attached to the wrist.

15. A measuring device as claimed in claim 13, characterized in that the sub-operating modes of the set mode (306) comprise manually set heart rate limits (504) and automatic determination of heart rate limits (502), the sub-operating modes being mutually exclusive sub-operating modes.

16. A measuring device as claimed in claim 13, characterized in that the sub-operating modes of the set mode (306) comprise: calculation of the energy consumed by the user (506).

17. A measuring device as claimed in claim 16, characterized in that the energy is expressed in kilocalories.

18. A measuring device as claimed in claim 13, characterized in that the sub-operating modes of the set mode (306) comprise: user settings (500).

19. A measuring device as claimed in claim 18, characterized in that the user settings (500) include at least one of the following: age, weight, sex of the user.

20. A measuring device as claimed in claim 13, characterized in that the sub-operating modes of the heart rate measurement mode (302) include at least one of the following: time taken up by the exercise and heart rate (400), real exercise time and heart rate (404), effective exercise time and heart rate (406), energy consumed by the user in the exercise and heart rate (410).

21. A measuring device as claimed in claim 13, characterized in that the operating modes comprise a file mode (304).

22. A measuring device as claimed in claim 21, characterized in that the control unit (112A) is so adapted that the loop sequence configured by the user affects the parameters to be stored by storage means (112C) in the heart rate measurement mode (302).

23. A measuring device as claimed in claim 21, characterized in that the sub-operating modes of the file mode (304) comprise at least one of the following: total exercise time, time between heart rate limits, energy consumed by the user in the exercise, cumulative energy consumed by the user.

24. A method of controlling a measuring device carried by a user during exercise for measuring non-invasively at least one signal from the body, the measuring device (102) comprising:

a control unit (112A) for controlling and monitoring the operation of the measuring device (102);

a measuring unit (104) communicating with the control unit (112A) for measuring at least one signal from the body;

a user interface (120) communicating with the control unit (112A) comprising:

selection means (114) for making selections, and various operating modes comprising at least a watch mode (300), a set mode (306), and at least one operating mode (302) for measuring a signal from the body, the operating modes being arranged as a main loop sequence (300-302-304-306), and the operating modes comprising various sub-operating modes for displaying parameters associated with exercising, the sub-operating modes being arranged as sub-loop sequences (400-404-406-410) under each operating mode, and display means (116, 122) for displaying data, and the sub-loop sequence (400-404-406-410) is displayed to the user by the display means (116, 122), characterized in that the user configures at least one sub-loop sequence (400-404-406-410), in which configuration at least one sub-operation mode (410) is by selection means (114) connected to be part of the sub-loop sequence (400-404-406-410) or sub-operation mode (410) is disconnected from the sub-loop sequence (400-404-406).

25. A method as claimed in claim 24, characterized in that a sub-operating mode (502) excludes another sub-operating mode (504).

26. A method as claimed in claim 24, characterized in that a new operating mode (308) is added to the main loop sequence (300-302-304-306).

27. A method as claimed in claim 24, characterized in that a new sub-operating mode (410) is added to the sub-loop sequence (400-404-406).

28. A method as claimed in claim 24, characterized in that the user utilizes the user interface (120) to configure the main loop sequence (300-302-304-306-308).

29. A method as claimed in claim 24, characterized in that the configuration is performed in the set mode (306).

30. A method as claimed in claim 24, characterized in that an ON/OFF type of configuration is performed for each sub-operating mode.

31. A method as claimed in claim 24, characterized in that the measuring device comprises short-cut means for fast selection of a sub-operating mode.

32. A method as claimed in claim 24, characterized in that the measuring device comprises home selection means for fast selection of the basic mode.

33. A method as claimed in claim 24, characterized in that the selection means (114) are push buttons (114A, 114B, 114C).

34. A method as claimed in claim 24, characterized in that the display means (116) are a liquid crystal display.

35. A method as claimed in claim 24, characterized in that the sub-operating modes of the watch mode (300) comprise: setting of alarm time, setting of time of day, setting of date.

36. A method as claimed in claim 24, characterized in that the signal to be measured is user heart rate, the operating mode measuring the signal from the body is heart rate measurement mode, and the measuring device is a heart rate monitor.

37. A method as claimed in claim 36, characterized in that the measuring unit (104) comprises a wireless transmitter (100) to be attached to the chest and a wireless heart rate receiver (110) to be attached to the wrist.

38. A method as claimed in claim 36, characterized in that the sub-operating modes of the set mode (306) comprise manually set heart rate limits (504) and automatic determination of heart rate limits (502), the sub-operating modes being mutually exclusive sub-operating modes.

39. A method as claimed in claim 36, characterized in that the sub-operating modes of the set mode (306) comprise: calculation of the energy consumed by the user (506).

40. A method as claimed in claim 39, characterized in that the energy is expressed in kilocalories.

41. A method as claimed in claim 36, characterized in that the sub-operating modes of the set mode (306) comprise: user settings (500).

42. A method as claimed in claim 41, characterized in that the user settings (500) include at least one of the following age, weight, sex of the user.

43. A method as claimed in claim 36, characterized in that the sub-operating modes of the heart rate measurement mode (302) include at least one of the following: time taken up by the exercise and heart rate (400), real exercise time and heart rate (404), effective exercise time and heart rate (406), energy consumed by the user in the exercise and heart rate (410).

44. A method as claimed in claim 36, characterized in that the operating modes comprise a file mode (306).

45. A method as claimed in claim 44, characterized in that the loop sequence configured by the user affects the parameters to be stored by storage means in the heart rate measurement mode (302).

46. A method as claimed in claim 45, characterized in that the sub-operating modes of the file mode (304) comprise at least one of the following: total exercise time, time between heart rate limits, energy consumed by the user in the exercise, cumulative energy consumed by the user.

* * * * *

UNITED STATES PATENT AND TRADEMARK OFFICE
CERTIFICATE OF CORRECTION

PATENT NO. : 6,361,502 B1
DATED : March 26, 2002
INVENTOR(S) : Puolakanaho et al.

It is certified that error appears in the above-identified patent and that said Letters Patent is hereby corrected as shown below:

Column 2,
Line 55, now reads "by the main groups"; should read -- by the main user groups --

Signed and Sealed this

Eighth Day of October, 2002

Attest:

Attesting Officer

JAMES E. ROGAN
Director of the United States Patent and Trademark Office